(12) United States Patent
Schwarz et al.

(10) Patent No.: US 8,998,928 B2
(45) Date of Patent: *Apr. 7, 2015

(54) CONFINEMENT OF KIDNEY STONE FRAGMENTS DURING LITHOTRIPSY

(71) Applicant: Genzyme Corporation, Cambridge, MA (US)

(72) Inventors: Alexander Schwarz, Brookline, MA (US); W. Scott McDougal, Manchester, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/779,415

(22) Filed: Feb. 27, 2013

(65) Prior Publication Data

US 2013/0172789 A1 Jul. 4, 2013

Related U.S. Application Data

(63) Continuation of application No. 12/946,478, filed on Nov. 15, 2010, now Pat. No. 8,409,218, which is a continuation of application No. 10/963,410, filed on Oct. 12, 2004, now abandoned.

(60) Provisional application No. 60/510,505, filed on Oct. 14, 2003.

(51) Int. Cl.
*A61B 17/22* (2006.01)
*A61B 17/225* (2006.01)
(Continued)

(52) U.S. Cl.
CPC ............ *A61B 17/225* (2013.01); *A61B 17/1204* (2013.01); *A61B 17/12045* (2013.01);
(Continued)

(58) Field of Classification Search
USPC ............. 601/2–4; 600/420, 431; 604/22, 113, 604/93.01; 606/127, 128
See application file for complete search history.

(56) References Cited

U.S. PATENT DOCUMENTS

| | | | |
|---|---|---|---|
| 4,308,905 | A | 1/1982 | Gallagher |
| 4,605,003 | A | 8/1986 | Oinuma et al. |

(Continued)

FOREIGN PATENT DOCUMENTS

| | | |
|---|---|---|
| EP | 0 64 5150 | 3/1995 |
| EP | 2 601 972 A2 | 6/2013 |

(Continued)

OTHER PUBLICATIONS

Hesse et al., "Study on the Prevalence and Incidence of Urolithiasis in Germany Comparing the Years 1979 vs. 2000" European Urology, (2003), vol. 44, No. 6, pp. 709-713.

(Continued)

*Primary Examiner* — Ruth S Smith
(74) *Attorney, Agent, or Firm* — Hamilton, Brook, Smith & Reynolds, P.C.

(57) ABSTRACT

The present invention improves significantly the success rate of lithotripsy and reduces the risk of tissue damage, by injecting a temporary plug in front, and optionally behind a concretion (for extracorporeal lithotripsy) or behind a concretion (for intracorporeal lithotripsy). One aspect of the present invention relates to injecting an inverse thermosensitive polymer solution into a lumen, thereby preventing the migration of a concretion, or its fragments, upon extracorporeal or intracorporeal lithotripsy.

20 Claims, 7 Drawing Sheets

(51) Int. Cl.
*A61B 17/12* (2006.01)
*A61F 2/01* (2006.01)

(52) U.S. Cl.
CPC ..... *A61B17/12099* (2013.01); *A61B 17/12186* (2013.01); *A61B 17/22012* (2013.01); *A61B 17/2202* (2013.01); *A61B 17/12022* (2013.01); *A61B 17/22022* (2013.01); *A61B 2017/12127* (2013.01); *A61B 2017/22021* (2013.01); *A61B 2017/22025* (2013.01); *A61B 2017/22054* (2013.01); *A61B 2017/22067* (2013.01); *A61B 2017/22082* (2013.01); *A61F 2/013* (2013.01)

(56) References Cited

U.S. PATENT DOCUMENTS

| | | | |
|---|---|---|---|
| 4,608,979 | A | 9/1986 | Breidenthal et al. |
| 4,696,297 | A | 9/1987 | Pleines et al. |
| 4,781,677 | A | 11/1988 | Wilcox |
| 4,845,125 | A | 7/1989 | Geier |
| 4,979,948 | A | 12/1990 | Geddes et al. |
| 5,059,200 | A | 10/1991 | Tulip |
| 5,129,910 | A | 7/1992 | Phan et al. |
| 5,397,302 | A | 3/1995 | Weaver et al. |
| 5,401,257 | A | 3/1995 | Chevalier, Jr. et al. |
| 5,403,324 | A | 4/1995 | Ciervo et al. |
| 5,448,363 | A | 9/1995 | Hager |
| 5,523,492 | A | 6/1996 | Emanuele et al. |
| 5,536,248 | A | 7/1996 | Weaver et al. |
| 5,567,859 | A | 10/1996 | Emanuele et al. |
| 5,599,299 | A | 2/1997 | Weaver et al. |
| 5,599,300 | A | 2/1997 | Weaver et al. |
| 5,696,298 | A | 12/1997 | Emanuele et al. |
| 5,722,980 | A | 3/1998 | Schulz et al. |
| 5,788,681 | A | 8/1998 | Weaver et al. |
| 5,800,711 | A | 9/1998 | Reeve et al. |
| 5,814,006 | A | 9/1998 | Planz |
| 5,843,028 | A | 12/1998 | Weaver et al. |
| 5,855,601 | A | 1/1999 | Bessler et al. |
| 5,860,872 | A | 1/1999 | Vitale |
| 5,860,972 | A | 1/1999 | Hoang |
| 6,149,656 | A | 11/2000 | Walz et al. |
| 6,159,220 | A | 12/2000 | Gobron et al. |
| 6,214,037 | B1 | 4/2001 | Mitchell et al. |
| 6,238,412 | B1 | 5/2001 | Dubrul et al. |
| 6,261,298 | B1 | 7/2001 | Irion et al. |
| 6,375,651 | B2 | 4/2002 | Grasso, III et al. |
| 6,440,061 | B1 | 8/2002 | Wenner et al. |
| 6,565,530 | B2 | 5/2003 | Sahatjian et al. |
| 6,620,172 | B1 | 9/2003 | Dretler et al. |
| 6,699,260 | B2 | 3/2004 | Dubrul et al. |
| 6,709,465 | B2 | 3/2004 | Mitchell et al. |
| 6,726,681 | B2 | 4/2004 | Grasso, III et al. |
| 6,761,824 | B2 | 7/2004 | Reeve et al. |
| 6,770,066 | B1 | 8/2004 | Weaver et al. |
| 6,949,125 | B2 | 9/2005 | Robertson |
| 7,039,453 | B2 | 5/2006 | Mullick et al. |
| 7,041,139 | B2 | 5/2006 | Bluni et al. |
| 7,052,489 | B2 | 5/2006 | Griego et al. |
| 7,104,983 | B2 | 9/2006 | Grasso, III et al. |
| 7,214,229 | B2 | 5/2007 | Mitchell et al. |
| 8,361,455 | B2 | 1/2013 | McDougal et al. |
| 8,409,218 | B2 * | 4/2013 | Schwarz et al. ............ 606/127 |
| 2002/0119116 | A1 | 8/2002 | Sahatjian et al. |
| 2002/0120237 | A1 | 8/2002 | Sahatjian et al. |
| 2003/0195464 | A1 | 10/2003 | Sahatjian et al. |
| 2004/0266983 | A1 | 12/2004 | Reeve et al. |
| 2005/0053662 | A1 | 3/2005 | Sahatjian et al. |
| 2005/0143678 | A1 | 6/2005 | Schwarz et al. |
| 2005/0175702 | A1 | 8/2005 | Muller-Schulte |
| 2005/0203498 | A1 | 9/2005 | Mon et al. |
| 2006/0269512 | A1 | 11/2006 | McDougal et al. |
| 2008/0269512 | A1 | 10/2008 | Lovis et al. |
| 2011/0060256 | A1 | 3/2011 | Schwarz et al. |
| 2013/0178866 | A1 | 7/2013 | McDougal et al. |
| 2014/0288569 | A1 | 9/2014 | McDougal et al. |

FOREIGN PATENT DOCUMENTS

| | | |
|---|---|---|
| WO | WO 92/16484 | 10/1992 |
| WO | WO 00/44323 | 8/2000 |
| WO | WO 02/067788 | 9/2002 |
| WO | WO 2005/037062 | 4/2005 |
| WO | WO 2006/119009 A1 | 11/2006 |

OTHER PUBLICATIONS

Lee et al., "Synthesis and Characterization of Thermosensitive Poly(organophosphazenes) with Methoxy-Poly(ethylene glycol) and Alkylamines as Side Groups" Bulletin Korean Chemical Society, (2002), vol. 23, No. 4, pp. 549-554.

March et al., "Pharmacokinetics of Adenoviral Vector-Mediated Gene Delivery to Vascular Smooth Muscle Cells: Modulation by Poloxamer 407 and Implication for Cardiovascular Gene Therapy" Human Gene Therapy, (1995), vol. 6, No. 1, pp. 41-53.

Database WPI, Section Ch, Week 2000059, Derwent Publications Ltd., London, GB; Class B04, AN 1995-175365, XP002397589 & JP 03 107488 B2 (Shiseido Co. Ltd.), Nov. 6, 2000, Abstract only.

International Search Report dated Sep. 25, 2006, from International Application No. PCT/US2006/016208.

International Search Report dated Feb. 13, 2006, from International Application No. PCT/US2004/033517.

Office Action dated Jul. 25, 2011, from U.S. Appl. No. 12/946,478.

Office Action dated Nov. 14, 2011, from U.S. Appl. No. 12/946,478.

Office Action dated May 21, 2012, from U.S. Appl. No. 12/946,478.

Notice of Allowance dated Nov. 28, 2012, from U.S. Appl. No. 12/946,478.

Dretler, S. P., "Prevention of Retrograde Stone Migration During Ureteroscopy", Nature Clinical Practice, 3(2):60-61 (2006).

Zeman, R.K., et al., "Cavitation Effects During Lithotripsy", Adiology, 177:157-161 (1990).

Zhu, S., et al., "The Role of Stress Waves and Cavitation in Stone Comminution in Shock Wave Lithotripsy", Ultrasound in Med. & Biol., 28(5):661-671 (2002).

Written Opinion for PCT/US2004/033517, "Confinement of Kidney-Stone Fragments During Lithotripsy", mailed Feb. 13, 2006.

International Preliminary Report on Patentability for PCT/US2004/033517, "Confinement of Kidney-Stone Fragments During Lithotripsy", issued Apr. 18, 2006.

Written Opinion for PCT/US2006/016208, "Non-Lithotripsic Kidney-Stone Therapy", mailed Sep. 25, 2006.

International Preliminary Report on Patentability for PCT/US2006/016208, "Non-Lithotripsic Kidney-Stone Therapy", issued Nov. 15, 2007.

Extended European Search Report for EP 12193441.8 "Non-Lithotripsic Kidney-Stone Therapy", dated Jul. 9, 2013.

Office Action for U.S. Appl. No. 11/412,407 "Non-Lithotripsic Kidney-Stone Therapy", mailed Apr. 20, 2009.

Notice of Allowance for U.S. Appl. No. 11/412,407 "Non-Lithotripsic Kidney-Stone Therapy", mailed Jan. 9, 2013.

Final Office Action for U.S. Appl. No. 11/412,407 "Non-Lithotripsic Kidney-Stone Therapy", mailed Aug. 13, 2010.

Final Office Action for U.S. Appl. No. 11/864,118, "Methods for Preventing Retropulsion of Concretions and Fragments During Lithotripsy", mailed Dec. 13, 2013.

Office Action for U.S. Appl. No. 11/864,118, "Methods for Preventing Retropulsion of Concretions and Fragments During Lithotripsy", mailed Feb. 26, 2013.

Final Office Action for U.S. Appl. No. 11/864,118, "Methods for Preventing Retropulsion of Concretions and Fragments During Lithotripsy", mailed Jul. 13, 2012.

Office Action for U.S. Appl. No. 11/864,118, "Methods for Preventing Retropulsion of Concretions and Fragments During Lithotripsy", mailed Nov. 9, 2011.

(56) References Cited

OTHER PUBLICATIONS

Final Office Action for U.S. Appl. No. 11/864,118, "Methods for Preventing Retropulsion of Concretions and Fragments During Lithotripsy", mailed Mar. 21, 2011.

Office Action for U.S. Appl. No. 11/864,118, "Methods for Preventing Retropulsion of Concretions and Fragments During Lithotripsy", mailed Sep. 13, 2010.

Office Action for U.S. Appl. No. 11/412,407 "Non-Lithotripsic Kidney-Stone Therapy", mailed Dec. 15, 2009.

Advisory Action for U.S. Appl. No. 11/412,407 "Non-Lithotripsic Kidney-Stone Therapy", mailed Nov. 22, 2010.

Examiner's Answer for U.S. Appl. No. 11/412,407 "Non-Lithotripsic Kidney-Stone Therapy", mailed Jun. 23, 2011.

Decision on Appeal for U.S. Appl. No. 11/412,407 "Non-Lithotripsic Kidney-Stone Therapy", mailed Apr. 27, 2012.

Office Action for U.S. Appl. No. 14/259,103 "Non-Lithotripsic Kidney-Stone Therapy", mailed Oct. 15, 2014.

* cited by examiner

CONFINEMENT OF KIDNEY STONE FRAGMENTS DURING LITHOTRIPSY

RELATED APPLICATIONS

This application is a continuation of U.S. application Ser. No. 12/946,478, filed Nov. 15, 2010, now U.S. Pat. No. 8,409,218, which is a continuation of U.S. application Ser. No. 10/963,410, filed Oct. 12, 2004, now abandoned, which claims the benefit of U.S. Provisional Application No. 60/510,505, filed on Oct. 14, 2003. The entire teachings of the above applications are incorporated herein by reference.

BACKGROUND OF THE INVENTION

The prevalence of urolithiasis, or kidney stone disease, is increasing with an aging population. A recent German epidemiology study showed an increase in the prevalence of kidney stones in the general German population from about 0.5% in 1971 to about 1.5% in 2000. (Hesse A. et al. European Urology 2003, 44, 709-713). Urolithiasis is also a significant health problem in the United States. It is estimated that between 5-10% of the general population will develop a urinary concretion during their lifetime. (Pak, C. T. Diseases of the Kidney, $5^{th}$ Edition; Boston; Little, Brown & Co.; 1993; pp. 729-743). The peak onset of urolithiasis is typically between 20 and 30 years of age, and males are effected more often then females.

Since being introduced in the 1980s, minimally invasive procedures such as lithotripsy, as well as ureteroscopy, have become the preferred methods for treatment in a majority of cases of concretions in the ureter, and have a potential for application to concretions that develop in other parts of the body such as the pancreas and the gallbladder. Lithotripsy is a medical procedure that uses energy in various forms such as acoustic shock waves, pneumatic pulsation, electrical hydraulic shock waves, or laser beams to break up biological concretions such as urinary calculi (e.g., kidney stones). The force of the energy, when applied either extracorporeally or intracorporeally, usually in focused and continuous or successive bursts, comminutes a kidney stone into smaller fragments that may be extracted from the body or allowed to pass through urination. Applications to other concretions formed in the body, such as pancreatic, salivary and biliary stones as well as the vascular system, are currently underway in several research laboratories across the United States and Europe.

As mentioned above, the introduction of extracorporeal shockwave lithotripsy (ESWL) in 1980 changed the management of renal and ureteral calculous disease from a surgical to a noninvasive procedure. ESWL is a procedure in which renal and ureteral calculi are broken up into smaller fragments by shock waves. These small fragments then can pass spontaneously. All shock wave generators are based on the geometrical principle of an ellipse. Shock waves are created at the first focal point of an ellipsoid ('F1'), within the half ellipse, and are directed towards the second focal point ('F2'), within the patient. The focal zone is the area at F2 where the shock wave is concentrated. The focal zone of the original Dornier HM3 exceeded 2 cm; most new electromagnetic generators have focal zones that average only 6 mm. The energy in these shock waves breaks a larger stone into smaller stones. This noninvasive approach allows patients to be rendered stone-free without surgical intervention or endoscopic procedures.

However there are several complications which can result from standard ESWL. Clinical experience demonstrates that a typical fragmentation rate of about 85%, and a stone-free rate of about 65-70%, is achievable with ESWL. A major problem with the procedure is that when kidney stones are fragmented the energy is sufficient to widely distribute them throughout the ureter and kidney. Further, fragments might become undetectable (e.g., too small to be imaged by fluoroscopy) but still too big to be easily passed. In addition, after the stones fragment, the shock wave treatment still focuses on the focal point F2, and the redistribution of the stones could move them outside the range of the treatment. Therefore, during the procedure it would be highly beneficial to confine the kidney stone and the resulting fragments into a narrow space within the focal point of F2. An improvement in this approach, which is described herein, would be to place a plug behind and in front of the stone, thereby confining the stone to a particular space. After the procedure the plugs could be removed and the smaller stones allowed to pass.

A different approach to the treatment of kidney stones is intracorporeal lithotripsy. A common approach employs laser energy at 2100 nm, generated by a holmium:YAG laser. A coumarin dye laser may also be used. The laser produces a vaporization bubble at the tip of the fiber optic and the energy is transferred to the stone and leads to fragmentation. However, proximal ureteral stone migration during laser lithotripsy accounts for a high percentage of ureteroscopic failures. In addition there is an electro-hydraulic technique, which utilizes electric discharge, ignited between two electrodes disposed within the probe and producing shock wave, expanding towards the concretion through liquid phase, which surrounds the concretion. Various mechanical anti-migration backstops have been developed and involve the placement of these devices behind the kidney stone, with respect to the laser or shock wave, and subsequent extraction of the smaller stones post fragmentation. A simpler approach, described herein, would be to introduce a temporary plug behind the stone, preventing the stone and its fragments from migrating further up the urethra or kidney. This approach would require a plug that was easily removable after the fragmentation.

It is an object of the invention to facilitate lithotripsy. The invention generally includes the use of a material (inverse thermosensitive polymers) that exists in liquid form and is transformed into a gel inside the body of a patient. The inverse thermosensitive polymers of the invention generally includes the use of a material that exists in liquid form at temperatures below about body temperature and as a gel at temperatures about at and above body temperature. The temperature at which the transition from liquid to gel occurs is referred to as the inverse thermosensitive polymer, and it can be a small temperature range as opposed to a specific temperature.

SUMMARY OF THE INVENTION

One aspect of the present invention relates to a method of lithotripsy comprising the steps of: injecting a first composition, comprising an inverse thermosensitive polymer, into a lumen of a mammal, at a first distance from a concretion, wherein said first composition does not contact said concretion; optionally injecting a second composition, comprising an inverse thermosensitive polymer, into said lumen, at a second distance from said concretion, wherein said second composition is placed on the approximately opposite side of said concretion relative to said first composition, wherein said second composition does not contact said concretion; and directing energy to said concretion causing the fragmentation of said concretion into a plurality of fragments.

In certain embodiments, the present invention relates to the aforementioned method, wherein said inverse thermosensitive polymer is a block copolymer, random copolymer, graft polymer, or branched copolymer.

In certain embodiments, the present invention relates to the aforementioned method, wherein said inverse thermosensitive polymer is a block polymer or a branched copolymer.

In certain embodiments, the present invention relates to the aforementioned method, wherein said inverse thermosensitive polymer is an optionally purified poloxamer or poloxamine.

In certain embodiments, the present invention relates to the aforementioned method, wherein said inverse thermosensitive polymer is optionally purified and selected from the group consisting of poloxamine 1107, poloxamine 1307, poloxamer 338 and poloxamer 407.

In certain embodiments, the present invention relates to the aforementioned method, wherein said inverse thermosensitive polymer is an optionally purified poloxamer 407.

In certain embodiments, the present invention relates to the aforementioned method, wherein said inverse thermosensitive polymer solution has a transition temperature of between about 10° C. and 40° C.

In certain embodiments, the present invention relates to the aforementioned method, wherein said inverse thermosensitive polymer solution has a transition temperature of between about 15° C. and 30° C.

In certain embodiments, the present invention relates to the aforementioned method, wherein said inverse thermosensitive polymer solution has a transition temperature of about 25° C.

In certain embodiments, the present invention relates to the aforementioned method, wherein said first distance is between about 1 cm and about 5 cm.

In certain embodiments, the present invention relates to the aforementioned method, wherein said first distance is between about 2 cm and about 4 cm.

In certain embodiments, the present invention relates to the aforementioned method, wherein said first distance is about 3 cm.

In certain embodiments, the present invention relates to the aforementioned method, wherein said second distance is between about 1 cm and about 5 cm.

In certain embodiments, the present invention relates to the aforementioned method, wherein said second distance is between about 2 cm and about 4 cm.

In certain embodiments, the present invention relates to the aforementioned method, wherein said second distance is about 3 cm.

In certain embodiments, the present invention relates to the aforementioned method, wherein said composition is injected into said lumen through a percutaneous access device.

In certain embodiments, the present invention relates to the aforementioned method, wherein said composition is injected into said lumen through a catheter or a syringe.

In certain embodiments, the present invention relates to the aforementioned method, wherein the catheter is a dual lumen catheter or a triple lumen catheter.

In certain embodiments, the present invention relates to the aforementioned method, wherein said energy is an acoustic shock wave, a pneumatic pulsation, an electrical hydraulic shock wave, or a laser beam.

In certain embodiments, the present invention relates to the aforementioned method, wherein said lumen is, or is part of, a kidney, a gall bladder, a ureter, a urinary bladder, a pancreas, a salivary gland, a small intestine or a large intestine.

In certain embodiments, the present invention relates to the aforementioned method, wherein said lumen is, or is part of, the ureter or kidney.

In certain embodiments, the present invention relates to the aforementioned method, wherein said concretion is a kidney stone, pancreatic stone, salivary stone, or biliary stone.

In certain embodiments, the present invention relates to the aforementioned method, wherein said concretion is a kidney stone.

In certain embodiments, the present invention relates to the aforementioned method, wherein said mammal is a human.

In certain embodiments, the present invention relates to the aforementioned method, wherein said composition comprises about 5% to about 30% of said inverse thermosensitive polymer.

In certain embodiments, the present invention relates to the aforementioned method, wherein said composition comprises about 10% to about 25% said inverse thermosensitive polymer.

In certain embodiments, the present invention relates to the aforementioned method, wherein said composition comprising an inverse thermosensitive polymer further comprises a contrast-enhancing agent.

In certain embodiments, the present invention relates to the aforementioned method, wherein said contrast-enhancing agent is selected from the group consisting of radiopaque materials, paramagnetic materials, heavy atoms, transition metals, lanthanides, actinides, dyes, and radionuclide-containing materials.

In certain embodiments, the present invention relates to the aforementioned method, wherein the inverse thermosensitive polymer has a polydispersity index from about 1.5 to 1.0.

In certain embodiments, the present invention relates to the aforementioned method, wherein the inverse thermosensitive polymer has a polydispersity index from about 1.2 to 1.0.

In certain embodiments, the present invention relates to the aforementioned method, wherein the inverse thermosensitive polymer has a polydispersity index from about 1.1 to 1.0.

In certain embodiments, the present invention relates to the aforementioned method, wherein said inverse thermosensitive polymer is an optionally purified poloxamer or poloxamine; and said inverse thermosensitive polymer solution has a transition temperature of between about 10° C. and 40° C.

In certain embodiments, the present invention relates to the aforementioned method, wherein said inverse thermosensitive polymer is an optionally purified poloxamer or poloxamine; and said inverse thermosensitive polymer solution has a transition temperature of between about 15° C. and 30° C.

In certain embodiments, the present invention relates to the aforementioned method, wherein said inverse thermosensitive polymer is an optionally purified poloxamer or poloxamine; and said inverse thermosensitive polymer solution has a transition temperature of about 25° C.

In certain embodiments, the present invention relates to the aforementioned method, wherein said energy is an acoustic shock wave, a pneumatic pulsation, an electrical hydraulic shock wave, or a laser beam; and said lumen is, or is part of, a kidney, a gall bladder, a ureter, a urinary bladder, a pancreas, a salivary gland, a small intestine or a large intestine.

In certain embodiments, the present invention relates to the aforementioned method, wherein said inverse thermosensitive polymer is optionally purified and selected from the group consisting of poloxamine 1107, poloxamine 1307, poloxamer 338 and poloxamer 407; and said lumen is, or is part of, a kidney, a gall bladder, a ureter, a urinary bladder, a pancreas, a salivary gland, a small intestine or a large intestine.

In certain embodiments, the present invention relates to the aforementioned method, wherein said inverse thermosensitive polymer is optionally purified poloxamer 407; and said lumen is, or is part of, the ureter or kidney.

In certain embodiments, the present invention relates to the aforementioned method, wherein said inverse thermosensitive polymer is optionally purified and selected from the group consisting of poloxamine 1107, poloxamine 1307, poloxamer 338 and poloxamer 407; wherein said energy is an acoustic shock wave, a pneumatic pulsation, an electrical hydraulic shock wave, or a laser beam; and said lumen is, or is part of, a kidney, a gall bladder, a ureter, a urinary bladder, a pancreas, a salivary gland, a small intestine or a large intestine.

In certain embodiments, the present invention relates to the aforementioned method, wherein said inverse thermosensitive polymer is an optionally purified poloxamer or poloxamine; said inverse thermosensitive polymer solution has a transition temperature of between about 10° C. and 40° C.; said energy is an acoustic shock wave, a pneumatic pulsation, an electrical hydraulic shock wave, or a laser beam; and said lumen is, or is part of, a kidney, a gall bladder, a ureter, a urinary bladder, a pancreas, a salivary gland, a small intestine or a large intestine.

In certain embodiments, the present invention relates to the aforementioned method, wherein said inverse thermosensitive polymer is an optionally purified poloxamer or poloxamine; wherein said inverse thermosensitive polymer solution has a transition temperature of between about 15° C. and 30° C.; said energy is an acoustic shock wave, a pneumatic pulsation, an electrical hydraulic shock wave, or a laser beam; and said lumen is, or is part of, a kidney, a gall bladder, a ureter, a urinary bladder, a pancreas, a salivary gland, a small intestine or a large intestine.

In certain embodiments, the present invention relates to the aforementioned method, wherein said inverse thermosensitive polymer is an optionally purified poloxamer or poloxamine; said inverse thermosensitive polymer solution has a transition temperature of about 25° C.; said energy is an acoustic shock wave, a pneumatic pulsation, an electrical hydraulic shock wave, or a laser beam; and said lumen is, or is part of, a kidney, a gall bladder, a ureter, a urinary bladder, a pancreas, a salivary gland, a small intestine or a large intestine.

In certain embodiments, the present invention relates to the aforementioned method, wherein said inverse thermosensitive polymer is an optionally purified poloxamer or poloxamine; said inverse thermosensitive polymer solution has a transition temperature of between about 10° C. and 40° C.; said energy is an electrical hydraulic shock wave; and said lumen is, or is part of, the ureter or kidney.

DETAILED DESCRIPTION OF THE INVENTION

Overview

The present invention improves significantly the success rate of lithotripsy and reduces the risk of tissue damage, by injecting temporary plugs in front and behind a concretion (external shock wave lithotripsy) or behind a concretion (intracorporeal lithotripsy). The present invention mitigates the risk of damage to surrounding body tissue when performing lithotripsy to removing organic material (e.g., biological concretions such as urinary, biliary, and pancreatic stones) which may obstruct or otherwise be present within the body's anatomical lumens. One aspect of the present invention relates to injecting an inverse thermosensitive polymer solution into a lumen, thereby preventing the migration of a concretion, or its fragments, during extracorporeal or intracorporeal lithotripsy. In one embodiment, the invention prevents the upward migration of concretion fragments generated during a fragmentation procedure. The invention also enables repeated or continuous application of energy to a concretion, and its resulting fragments, or other biological and non-biological/foreign material, while minimizing trauma to the surrounding tissue. The present invention improves significantly the success rate of lithotripsy, reduces the risk of tissue damage, and decreases the procedure time.

Figure 1:
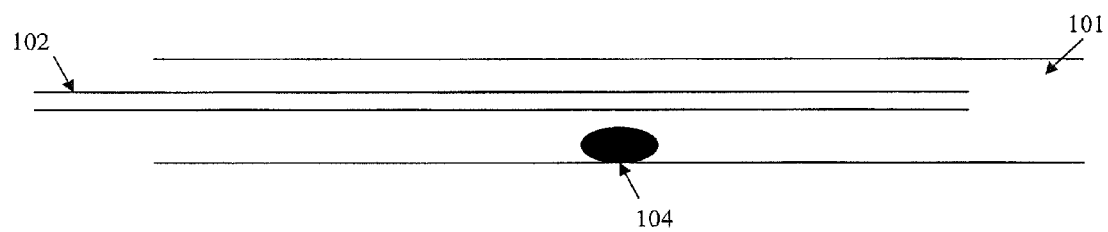
FIG. 1 depicts the deployment of a catheter into a lumen containing a concretion.
Figure 2:
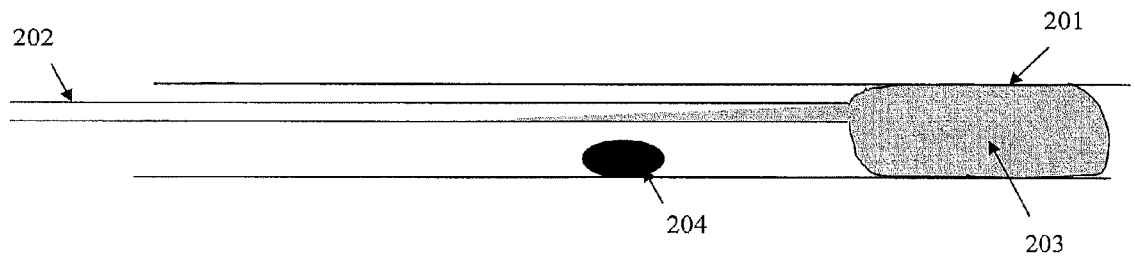
FIG. 2 depicts the deployment of a thermosensitive polymer composition and the formation of a plug behind the concretion.
Figure 3:
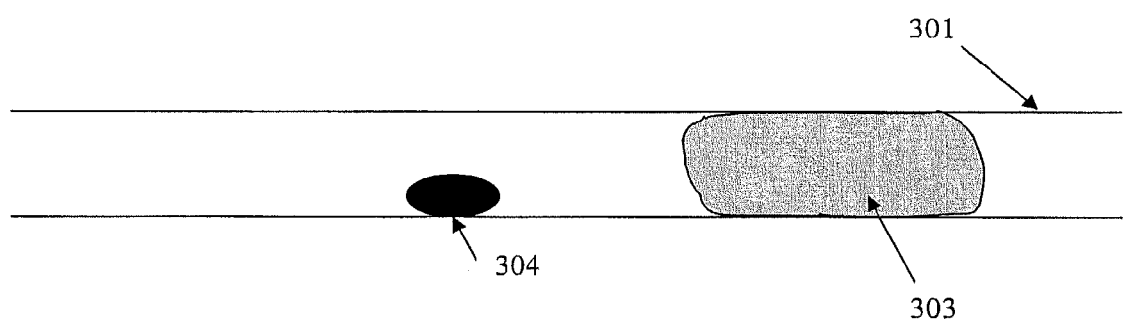
FIG. 3 depicts the position of the gel (plug) and concretion before lithotripsy.
Figure 4:
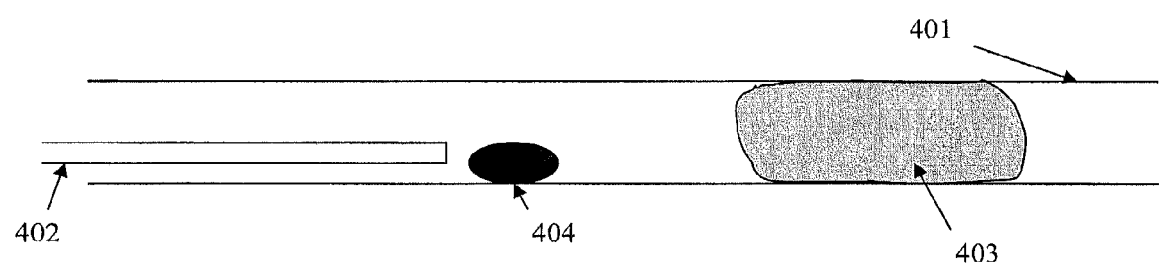
FIG. 4 depicts the deployment of a lithotripsy probe for intracorporeal lithotripsy.

In one illustrative embodiment according to the disclosure a thermosensitive polymer is placed within a lumen at a distance from a concretion to improve the success rate of a lithotripsy procedure while reducing the risk of tissue damage. As shown in FIG. 1, a catheter 102 is deployed into a lumen 101 containing a concretion 104. A thermosensitive polymer 203 is placed within the lumen 201 using the catheter 202 at a selected distance from the concretion 204 as depicted in FIG. 2. As depicted in FIG. 3, the placement of the thermosensitive polymer 303, prior to a lithotripsy procedure, forms a gel plug 303 within the lumen 301, when the thermosensitive polymer is at or about normal body temperature. The placement of the gel plug 303 prevents applied shock waves, or other energy forces, to the concretion 304 from being dampened or diverted. According to the disclosure, a lithotripsy probe 402 is inserted within the lumen 401 to fragment the concretion 404 as shown in FIG. 4. The gel plug 403 prevents applied energy from being dampened or diverted from the concretion 404.

Figure 5:
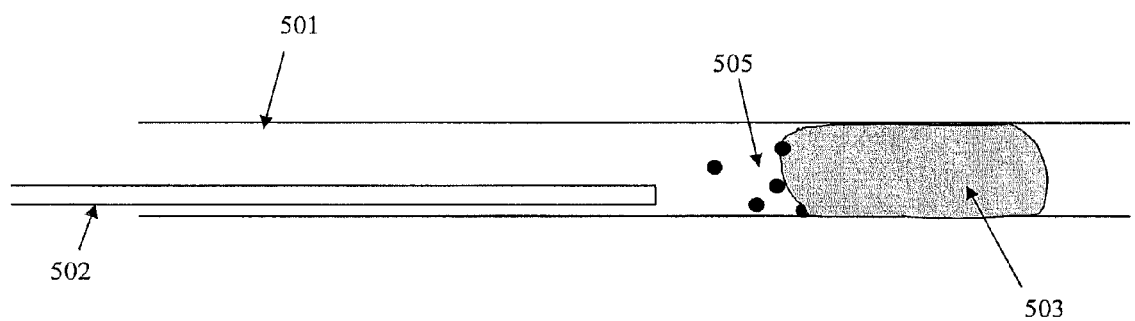
FIG. 5 depicts the result of fragmentation of the concretion, wherein the concretion fragments are prevented from widely distributing through out the kidney.
Figure 6:
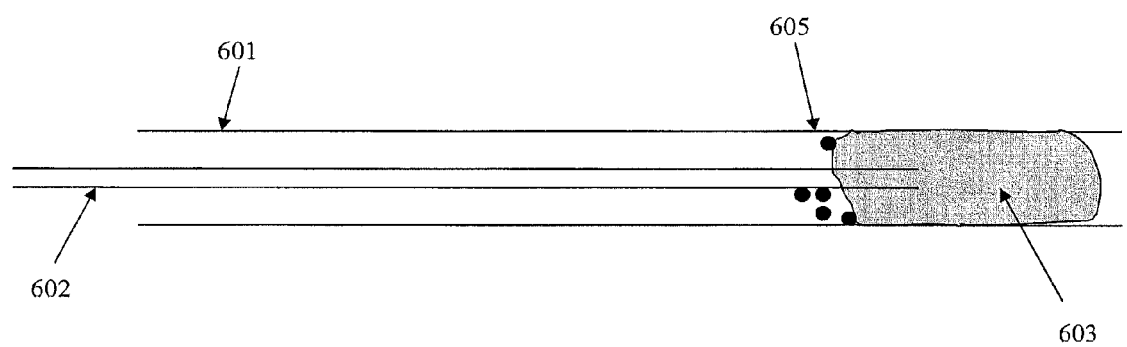
FIG. 6 depicts the dissolution of the gel (plug) via the injection of a saline solution into the gel via a catheter.
Figure 7:
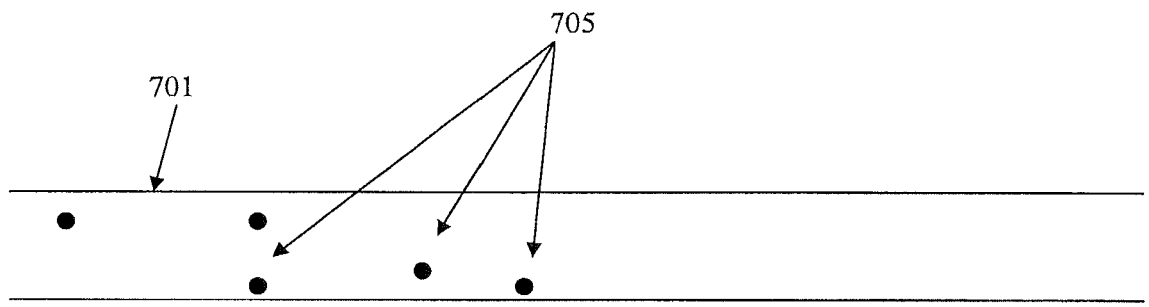
FIG. 7 depicts the ureter after the dissolution of the gel (plug), with small concretion fragments which can easily be passed.

In another illustrative embodiment energy is applied to the concretion through the lithotripsy probe 502. The applied energy results in the concretion breaking into fragments 505 that are prevented from widely distributing throughout the kidney by the gel plug 503 placed within the lumen 501, as shown in FIG. 5. After energy is applied and the concretion is broken into fragments the gel plug 603 within the lumen 601 is dissolved by the injection of a low temperature saline solution into the gel plug 603 through a catheter 602, as depicted in FIG. 6. The injection of the low temperature saline solution dissolves the gel plug allowing small concretion fragments 705 to pass through the lumen 701 as shown in FIG. 7.

DEFINITIONS

For convenience, certain terms employed in the specification, exemplification, and appended claims are collected here.

The articles "a" and "an" are used herein to refer to one or to more than one (i.e., to at least one) of the grammatical object of the article. By way of example, "an element" means one element or more than one element.

The terms "reversibly gelling" and "inverse thermosensitive" refer to the property of a polymer wherein gelation takes place upon an increase in temperature, rather than a decrease in temperature.

The term "transition temperature" refers to the temperature or temperature range at which gelation of an inverse thermosensitive polymer occurs.

The term "contrast-enhancing" refers to materials capable of being monitored during injection into a mammalian subject by methods for monitoring and detecting such materials, for example by radiography or fluoroscopy. An example of a contrast-enhancing agent is a radiopaque material. Contrast-enhancing agents including radiopaque materials may be either water soluble or water insoluble. Examples of water soluble radiopaque materials include metrizamide, iopamidol, iothalamate sodium, iodomide sodium, and meglumine Examples of water insoluble radiopaque materials include metals and metal oxides such as gold, titanium, silver, stainless steel, oxides thereof, aluminum oxide, zirconium oxide, etc.

As used herein, the term "polymer" means a molecule, formed by the chemical union of two or more oligomer units. The chemical units are normally linked together by covalent linkages. The two or more combining units in a polymer can be all the same, in which case the polymer is referred to as a homopolymer. They can be also be different and, thus, the polymer will be a combination of the different units. These polymers are referred to as copolymers.

The term "biocompatible", as used herein, refers to having the property of being biologically compatible by not producing a toxic, injurious, or immunological response in living tissue.

The term "poloxamer" denotes a symmetrical block copolymer, consisting of a core of PPG polyoxyethylated to both its terminal hydroxyl groups, i.e. conforming to the interchangeable generic formula $(PEG)_X$-$(PPG)_Y$-$(PEG)_X$ and $(PEO)_X$—$(PPO)_Y$—$(PEO)_X$. Each poloxamer name ends with an arbitrary code number, which is related to the average numerical values of the respective monomer units denoted by X and Y.

The term "poloxamine" denotes a polyalkoxylated symmetrical block copolymer of ethylene diamine conforming to the general type $[(PEG)_X$-$(PPG)_Y]_2$-$NCH_2CH_2N$—$[(PPG)_Y$-$(PEG)_X]_2$. Each Poloxamine name is followed by an arbitrary code number, which is related to the average numerical values of the respective monomer units denoted by X and Y.

The term "inverse thermosensitive polymer" as used herein refers to a polymer that is soluble in water at ambient temperature, but at least partially phase-separates out of water at physiological temperature. Inverse thermosensitive polymers include poloxamer 407, poloxarner 188, Pluronic® F127, Pluronic® F68, poly(N-isopropylacrylamide), poly(methyl vinyl ether), poly(N-vinylcaprolactam); and certain poly(organophosphazenes). See Bull. Korean Chem. Soc. 2002, 23, 549-554.

The phrase "polydispersity index" refers to the ratio of the "weight average molecular weight" to the "number average molecular weight" for a particular polymer; it reflects the distribution of individual molecular weights in a polymer sample.

The phrase "weight average molecular weight" refers to a particular measure of the molecular weight of a polymer. The weight average molecular weight is calculated as follows: determine the molecular weight of a number of polymer molecules; add the squares of these weights; and then divide by the total weight of the molecules.

The phrase "number average molecular weight" refers to a particular measure of the molecular weight of a polymer. The number average molecular weight is the common average of the molecular weights of the individual polymer molecules. It is determined by measuring the molecular weight of n polymer molecules, summing the weights, and dividing by n.

The term "concretion" denotes a mass or nodule of solid matter formed by growing together, by congelation, condensation, coagulation, induration, etc. Common synonyms, for example, are stones, clots, tones, lumps or calculi. Often, biologically, a concretion is a hard lump of mineral salts found in a hollow organ or duct of the body. In one embodiment, concretion refers to stone-like objects found within a body organ (e.g., the kidneys).

The term "lumen" denotes the space enclosed by a tube-like structure or hollow organ, such as inside an artery, a vein, a kidney, a gall bladder, a ureter, a urinary bladder, a pancreas, a salivary gland, a small intestine or a large intestine (i.e., an opening, space, or cavity in a biological system).

Concretions

Concretions can develop in certain parts of the body, such as in the kidneys, pancreas, ureter and gallbladder. It is not uncommon for biological concretions to be referred to as calculi or stones, especially when they are composed of mineral salts. For example, concretions formed in the biliary system are called gallstones. Those that form in the bladder are as also known as vesical calculi or bladder stones, and cystoliths. Calculi occurring in the kidney are often called kidney stones. Calculi can also occur in the ureter and are usually the result of the passage of one originating in the kidney. Calculi of the urinary bladder; also known as vesical calculi or bladder stones, and cystoliths. It is also possible to observe the presence of calculi in a salivary ducts or glands.

There are four main types of calculi observed biologically. The majority of calculi, about 75%, are calcium-containing, composed of calcium oxalate, sometimes mixed with calcium phosphate. Another 15% are composed of magnesium ammonium phosphate; these calculi are often referred to as "triple stones" or struvite stones. The bulk of the remaining stones are made up of uric acid or cystine. When these calculi are too large to pass spontaneously, medical intervention is often needed.

Lithotripsy

Larger biological concretions often need to be shattered because their size prohibits non-surgical removal from the body. This procedure is known as lithotripsy. Shattering a concretion (by, for example, light, chemical, or physical energy) will disperse the resulting fragments from the original location of the concretion. It is important to remove all the fragments, as fragments that are not removed from the body can form the nuclei for the formation of new concretions. This process is made difficult by the fact that often the shattering process can cause fragments to move into inaccessible or unknown areas of the body thus preventing or interfering with the capture and removal of the fragments.

It is common to refer to lithotripsy with respect to where the energy is generated. Extracorporeal lithotripsy is where the energy needed is generated outside the body; intracorporeal lithotripsy is where the energy needed is generated inside the body; both methods are discussed in more detail below.

Extracorporeal Lithotripsy

In one embodiment, energy transferred to fragment a concretion may emanate from outside the patient's body, from a lithotriptor for example, and travel through the patient's body until reaching the concretion targeted for fragmentation in a process called extracorporeal shock wave lithotripsy (ESWL). ESWL is a method of stone fragmentation commonly used to treat kidney stone disease. Various lithotriptors and methods exist for generating high-intensity, focused shock waves for the fragmentation of objects, such as kidney stones, inside a human being and confined in a body liquid. A lithotriptor generating a spark gap discharge in water has been used to generate a shock wave within an ellipsoidal reflector, which couples and focuses the shock wave to fragment kidney stones inside the patient's body. Lithotriptors also exist that use a coil and a mating radiator, in the form of a spherical segment, to produce magnetically induced self-converging shock waves that can be directed at a stone within the patient's body. A lithotriptor also exists that features piezoelectric elements arranged in mosaic form on a spheroidal cap have also been used to produce focused high-intensity shock waves at the geometric center of the cap, where the concretion must be placed.

The treatment of concretion ailments by means of an extracorporeal lithotripsy apparatus requires some means, such an ultrasound locating system, for correctly positioning the lithotripsy apparatus and the patient relative to each other so that the concretion, such as a kidney stone, is located in the focus of the shock waves. The focused shock waves are then coupled into the body of the patient, and act on the concretion to disintegrate it into fragments, which can be naturally eliminated.

As mentioned above, a locating system is also needed to identifying the position of the concretion within the patient, such as an x-ray system or an ultrasound system. A visual display is provided by the locating system which includes a mark identifying the concretion and an indicator for the position of the focus. Devices of this type are utilized, for example, for disintegrating kidney stones in situ in the human body, and have the advantage of avoiding invasion of the body using instruments.

Intracorporeal Lithotripsy

Intracorporeal lithotripsy utilizes a probe advanced with the aim of endoscope and positioned in proximity to the concretion. The energy, required for fragmentation is transferred through the probe to the concretion and the treatment process is visualized during fragmentation. The mode of energy transfer may be different and accordingly the intracorporeal lithotripsy techniques are divided into following groups: ultrasonic, laser, electro-hydraulic and mechanic/ballistic impact.

The last group comprises, for example, detonating an explosive near the concretion and causing the shock wave generated by the explosion to act directly upon the concretion and crush it into pieces. An example of such technique is disclosed in U.S. Pat. No. 4,605,003, referring to a lithotriptor comprising an inner tube inserted within an outer slender tube and provided with an explosive layer or a gas-generating layer. By the blasting of the explosive layer or the gas-generating layer, the outer slender tube or the inner tube is caused to collide with the stone and crush it.

An example of mechanical impact technique can be found in U.S. Pat. No. 5,448,363 in which is disclosed an endoscopic lithotriptor provided with a hammer element to periodically strike the concretion. The hammer element is pneumatically driven by a linear jet of air causing it to swing through an arc about a pivot to impact an anvil. There are known also many other patents, disclosing lithotriptors, which operation is based on mechanic/ballistic principle, e.g. U.S. Pat. No. 5,722,980 and U.S. Pat. No. 6,261,298.

An example of laser technique is a multi-purpose lithotriptor, equipped with laser light-conducting fibers, through which the energy required for crushing the concretion is conducted.

Ultrasonic technique is relatively popular and because of its safety and usefulness is widely accepted. According to this principle ultrasound probe emits high-frequency ultrasonic energy that has a disruption effect upon direct exposure to the concretion. Direct contact of the probe tip and stone is essential for effectiveness of ultrasonic lithotripsy. This technique is implemented in many lithotriptors, e.g. as described in U.S. Pat. No. 6,149,656.

In addition there is electro-hydraulic technique, which utilizes electric discharge, ignited between two electrodes disposed within the probe and producing shock wave, expanding towards the concretion through liquid phase, which surrounds the concretion. In the literature electro-hydraulic lithotripsy is defined as the oldest form of "power" lithotripsy. The electro-hydraulic lithotriptor releases high-energy impulse discharges from an electrode at the tip of a flexible probe, which is placed next to the stone. It is considered a highly effective means of bladder stone shattering and has become an accepted practice for this use. Since the shock waves generated during electro-hydraulic lithotripsy treatment are of sufficient force the probe must not be used 5 mm or closer to soft tissues otherwise severe damage will result. Since the discharge takes place within liquid phase the concretion is destroyed by virtue of combination of energy of the shock wave, caused by the discharge, hydraulic pressure of the surrounding liquid and collision of fragments in the liquid flow.

Problems with Conventional Lithotripsy

It can be easily appreciated that in lithotripsy the energy is transferred indirectly to the concretion via a liquid medium. Therefore the amount of energy required for fragmentation must be sufficient to overcome the strength of the concretion, to cause its fragmentation, after the energy has been delivered through the working liquid. For a concretion encased in a polymer matrix, even more additional energy will be needed. Unfortunately, release of such high levels of energy by producing shock waves might be harmful to the adjacent tissues and therefore potentially dangerous for the patient.

Another problem of almost all lithotriptors that are intended for destroying concretions by bringing mechanical energy of impact or shock wave is the fact that the stone is usually "displaced" with each pulse of energy, leaving the previous place and being "thrown" to another one. This renders the operation complicate and may cause mechanical damage to the surrounding tissue. The instant invention solves both of these problems.

Methods of the Invention

The present invention improves significantly the success rate of lithotripsy and reduces the risk of tissue damage, by injecting temporary plugs in front and behind a concretion (external shock wave lithotripsy) or behind a concretion (intracorporeal lithotripsy) prior to the fragmentation of the concretion. The plugs in both applications consist of an aqueous solution of inverse thermosensitive polymers. These polymer solutions are liquid below body temperature and gel at about body temperature. The polymer solution starts externally of the body and thus at a temperature below body temperature. The polymer solution may be further chilled to prolong the time the gel stays in the liquid form. A preferred temperature is about 10° C. below the gelation temperature of the polymer solution.

Introduction/Removal of the Plug

The polymer solution can be introduced through a catheter behind and in front of the concretion for extracorporeal shockwave lithotripsy approach, and just behind the concretion for the intracorporeal lithotripsy approach. In one embodiment, a catheter can be used to dispense one or more fluids other than or in addition to the inverse thermosensitive polymer. The catheter also can be a dilatation catheter with the ability also to dispense one or more fluids other than or in addition to the polymer. In one embodiment, the catheter is 3-10 French in size, and more preferably 3-6 French.

In another embodiment the catheter may be a triple lumen catheter with one lumen for the delivery of the polymer solution behind the kidney stone, one lumen for the delivery of the polymer solution in front of the kidney stone and one lumen for the delivery of other fluids like contrast agent solution, saline or for the delivery of a solution to dissolved the gel after the procedure.

In another embodiment, the syringe or other mechanism used to inject the inverse thermosensitive polymer in liquid form into the body can be, for example, a 1-100 cc syringe such as a syringe with volume of 1-50 cc or with a volume of 1-5 cc. Pressure applied to the syringe can be applied by hand or by an automated syringe pusher.

The gelation of reverse thermosensitive polymers is dependent on the temperature and the concentration of the polymer. Therefore, after the fragmentation procedure, the gel can be removed by instilling a fluid around the gel, which leads to dissolution of the gel. The fluid may be chilled to help in the dissolution with a preferred temperature of about 10° C. below the gelation temperature. The fluid can be instilled through a catheter or syringe percutaneously.

Inverse Thermosensitive Polymers

In general, the inverse thermosensitive polymers used in the methods of the invention, which become a gel at or about body temperature, can be injected into the patient's-body in a liquid form. The injected material once reaching body temperature undergoes a transition from a liquid to a gel. The inverse thermosensitive polymers used in connection with the methods of the invention may comprise a block copolymer with inverse thermal gelation properties. The block copolymer can further comprise a polyoxyethylene-polyoxypropylene block copolymer such as a biodegradable, biocompatible copolymer of polyethylene oxide and polypropylene oxide. Also, the inverse thermosensitive polymer can include a therapeutic agent such as an anti-angiogenic agent.

The molecular weight of the inverse thermosensitive polymer is preferably between 1,000 and 50,000, more preferably between 5,000 and 35,000. Preferably the polymer is in an aqueous solution. For example, typical aqueous solutions contain about 5% to about 30% polymer, preferably about 10% to about 25%. The molecular weight of a suitable inverse thermosensitive polymer (such as a poloxamer or poloxamine) may be, for example, between 5,000 and 25,000, and more particularly between 7,000 and 20,000.

The pH of the inverse thermosensitive polymer formulation administered to the mammal is, generally, about 6.0 to about 7.8, which are suitable pH levels for injection into the mammalian body. The pH level may be adjusted by any suitable acid or base, such as hydrochloric acid or sodium hydroxide.

Suitable inverse thermosensitive polymers include polyoxyethylene-polyoxypropylene (PEO-PPO) block copolymers. Two examples are Pluronic® F127 and F108, which are PEO-PPO block copolymers with molecular weights of 12,600 and 14,600, respectively. Each of these compounds is available from BASF of Mount Olive, N.J. Pluronic® F108 at 12-25% concentration in phosphate buffered saline (PBS) is an example of a suitable inverse thermosensitive polymeric material. Pluronic® acid F127 at 12-25% concentration in PBS is another example of a suitable material. Low concentrations of dye (such as crystal violet), hormones, therapeutic agents, fillers, and antibiotics can be added to the inverse thermosensitive polymer. In general, other biocompatible, biodegradable PEO-PPO block copolymers that exist as a gel at body temperature and a liquid at below body temperature may also be used according to the present invention.

Notably, Pluronic® polymers have unique surfactant abilities and extremely low toxicity and immunogenic responses. These products have low acute oral and dermal toxicity and low potential for causing irritation or sensitization, and the general chronic and sub-chronic toxicity is low. In fact, Pluronic® polymers are among a small number of surfactants that have been approved by the FDA for direct use in medical applications and as food additives (BASF (1990) Pluronic® & Tetronic® Surfactants, BASF Co., Mount Olive, N.J.). Recently, several Pluronic® polymers have been found to enhance the therapeutic effect of drugs, and the gene transfer efficiency mediated by adenovirus. (March K L, Madison J E, Trapnell B C, "Pharmacokinetics of adenoviral vector-mediated gene delivery to vascular smooth muscle cells: modulation by poloxamer 407 and implication for cardiovascular gene therapy" Hum Gene Therapy 1995, 6, 41-53).

The average molecular weights of the poloxamers range from about 1,000 to greater than 16,000 daltons. Because the poloxamers are products of a sequential series of reactions, the molecular weights of the individual poloxamer molecules form a statistical distribution about the average molecular weight. In addition, commercially available poloxamers contain substantial amounts of poly(oxyethylene) homopolymer and poly(oxyethylene)/poly(oxypropylene) diblock polymers. The relative amounts of these byproducts increase as the molecular weights of the component blocks of the poloxamer increase. Depending upon the manufacturer, these byproducts may constitute from about 15 to about 50% of the total mass of the polymer.

The inverse thermosensitive polymers may be purified using a process for the fractionation of water-soluble polymers, comprising the steps of dissolving a known amount of the polymer in water, adding a soluble extraction salt to the polymer solution, maintaining the solution at a constant optimal temperature for a period of time adequate for two distinct phases to appear, and separating physically the phases. Additionally, the phase containing the polymer fraction of the preferred molecular weight may be diluted to the original volume with water, extraction salt may be added to achieve the original concentration, and the separation process repeated as needed until a polymer having a narrower molecular weight distribution than the starting material and optimal physical characteristics can be recovered.

In certain embodiments, a purified poloxamer or poloxamine has a polydispersity index from about 1.5 to about 1.0. In certain embodiments, a purified poloxamer or poloxamine has a polydispersity index from about 1.2 to about 1.0. In certain embodiments, a purified poloxamer or poloxamine has a polydispersity index from about 1.1 to about 1.0.

The aforementioned process consists of forming an aqueous two-phase system composed of the polymer and an appropriate salt in water. In such a system, a soluble salt can be added to a single phase polymer-water system to induce phase separation to yield a high salt, low polymer bottom phase, and a low salt, high polymer upper phase. Lower molecular weight polymers partition preferentially into the high salt, low polymer phase. Polymers that can be fractionated using this process include polyethers, glycols such as poly(ethylene glycol) and poly(ethylene oxide)s, polyoxyalkylene block copolymers such as poloxamers, poloxamines, and polyoxypropylene/polyoxybutylene copolymers, and other polyols, such as polyvinyl alcohol. The average molecular weight of these polymers may range from about 800 to greater than 100,000 daltons. See U.S. Pat. No. 6,761,824. The aforementioned purification process inherently exploits the differences in size and polarity, and therefore solubility, among the poloxamer molecules, the poly(oxyethylene) homopolymer and the poly(oxyethylene)/poly(oxypropylene) diblock byproducts. The polar fraction of the poloxamer, which generally includes the lower molecular weight fraction and the byproducts, is removed allowing the higher molecular weight fraction of poloxamer to be recovered. The larger molecular weight poloxamer recovered by this method has physical characteristics substantially different from the starting material or commercially available poloxamer including a higher average molecular weight, lower polydispersity and a higher viscosity in aqueous solution.

Other purification methods may be used to achieve the desired outcome. For example, WO 92/16484 discloses the use of gel permeation chromatography to isolate a fraction of poloxamer 188 that exhibits beneficial biological effects, without causing potentially deleterious side effects. The copolymer thus obtained had a polydispersity index of 1.07 or less, and was substantially saturated. The potentially harmful side effects were shown to be associated with the low molecular weight, unsaturated portion of the polymer, while the medically beneficial effects resided in the uniform higher molecular weight material. Other similarly improved copolymers were obtained by purifying either the polyoxypropylene center block during synthesis of the copolymer, or the copolymer product itself (e.g., U.S. Pat. No. 5,523,492 and U.S. Pat. No. 5,696,298).

Further, a supercritical fluid extraction technique has been used to fractionate a polyoxyalkylene block copolymer as disclosed in U.S. Pat. No. 5,567,859. A purified fraction was obtained, which was composed of a fairly uniform polyoxyalkylene block copolymer having a polydispersity of less than 1.17. According to this method, the lower molecular weight fraction was removed in a stream of carbon dioxide maintained at a pressure of 2200 pounds per square inch (psi) and a temperature of 40° C.

Additionally, U.S. Pat. No. 5,800,711 discloses a process for the fractionation of polyoxyalkylene block copolymers by the batchwise removal of low molecular weight species using a salt extraction and liquid phase separation technique. Poloxamer 407 and poloxamer 188 were fractionated by this method. In each case, a copolymer fraction was obtained which had a higher average molecular weight and a lower polydispersity index as compared to the starting material. However, the changes in polydispersity index were modest and analysis by gel permeation chromatography indicated that some low-molecular-weight material remained. The viscosity of aqueous solutions of the fractionated polymers was significantly greater than the viscosity of the commercially available polymers at temperatures between 10° C. and 37° C., an important property for some medical and drug delivery applications. Nevertheless, some of the low molecular weight contaminants of these polymers are thought to cause deleterious side effects when used inside the body, making it especially important that they be removed in the fractionation process. As a consequence, polyoxyalkylene block copolymers fractionated by this process are not appropriate for all medical uses.

In a preferred embodiment, the polymers used are block polymers such as polyoxyethylene-polyoxypropylene (PEO-PPO) block polymers of the general structure A-B, (A-B)$_n$, A-B-A (e.g., Pluronic®), or (A-B-A)$_n$ with A being the PEO part and B being the PPO part and n being greater than 1. In another preferred embodiment, the polymers used are branched polymers of polyoxyethylene-polyoxypropylene (PEO-PPO) like tetra-functional poloxamines (e.g., Tetronic®).

EXEMPLIFICATION

Example 1

Gelation Temperature of Selected Pluronic® and Tetronic® Polymer Solutions

The polymer was weighed into a plastic tube. To achieve the required concentration the weight was multiplied by 4, for 25 weight percent (w %), and by 5, for 20 weight percent (w %), and the required final weight was achieved by adding saline. The solutions were placed in the fridge at 4° C. and usually were ready the next morning. Gelation points were measures in a Brookfield viscometer and the point at which viscosity exceeded the range of the plate/cone (>102,000 cP) was called the gelation temperature.

TABLE 1

Gelation Temperature of Selected Inverse Thermosensitive Polymer Solutions in Saline

| Polymer | Concentration | Temperature |
| --- | --- | --- |
| Tetronic 1107 | 25 w % | 27° C. |
| Tetronic 1107 | 20 w % | 34° C. |
| Purified Tetronic 1107 | 25 w % | 22° C. |
| Purified Tetronic 1107 | 20 w % | 32.5° C. |
| Tetronic 1307 | 25 w % | 24.5° C. |
| Tetronic 1307 | 20 w % | 31° C. |
| Purified Tetronic 1307 | 25 w % | 20° C. |
| Purified Tetronic 1307 | 20 w % | 26° C. |
| Pluronic F108 | 25 w % | 26° C. |
| Pluronic F108 | 20 w % | 60° C. |
| Purified Pluronic F108 | 25 w % | 19° C. |
| Purified Pluronic F108 | 20 w % | 26 |

Example 2

Gelation Temperature of Selected Pluronic® and Tetronic® Polymer Solutions with Iodinated Contrast Agent Purified polymers were weighed into 50 mL centrifuge tubes and a 1:1 mixture of saline and 100% Omnipaque 300 were added until a specific weight percentage was reached. Gelation points were measured in a Brookfield viscometer and the point at which the viscosity exceeded the range of the plate/cone (>102,000 cP) was called the gelation point. All solutions were further heated to 37° C. to ascertain that the material still exceeded the viscosity range and remained a gel. All gels passed.

TABLE 2

Gelation Temperature of Purified Inverse Thermosensitive Polymer Solutions containing 50 w % Omnipaque 300

| Polymer | Concentration | Temperature |
| --- | --- | --- |
| Purified Tetronic 1107 | 20 w % | 24° C. |
| Purified Tetronic 1307 | 21 w % | 26.5° C. |
| Purified Tetronic F108 | 18 w % | 21.5° C. |
| Purified Tetronic F127 | 18 w % | 18° C. |

Example 3

Plastic Tube Experiments

A plastic tube with an inner diameter of 0.9 cm was used as a mimic of a ureter. The tube was partially filled with saline and the kidney stone placed into the middle of the tube. A ureteroscope was placed inside the tube close to the stone and cold polymer solutions were injected behind the stone. The stone was fragmented using either electro-hydraulic lithotripsy or laser lithotripsy. Various inverse thermosensitive polymer solutions such as purified Pluronic F108 (poloxamer 338), Pluronic F127 (poloxamer 407) and Tetronic 1307, were tested in this set-up in concentrations ranging from 15 to 25 w %. In all cases, the stone could be fragmented into smaller particles and the gel captures all fragments. The lower polymer concentrations (15 w %) resulted in rather soft gels, while the higher polymer concentrations (25 w %) were difficult to deploy due to the increased viscosity of the polymer solution and early onset of gelation.

Example 4

Pig Ureter Experiments

Pig ureters (approximately 25 cm in length) were fixed to a tray and the tray submerged in a water bath heated to 37° C. A sheath was inserted into the ureter and a small (approximately 5 mm) Plaster of Paris kidney stone mimic was advanced into the ureter through the sheath using a stone basket. A 3F catheter was advanced through the working channel of the ureteroscope approximately 3 cm behind the stone and 1.5 mL of a 20 w % purified Pluronic F127 (poloxamer 407) solution was injected. The poloxamer gel was colored blue with methylene blue. Irrigation of the ureter was accomplished with room temperature saline at a flow rate of approximately 5 mL/minute. Very little dilution of the gel was observed during the 20 minutes of irrigation as the gelation temperature of the gel is about 15° C. Dissolution was easily accomplished by injection into the gel with either room temperature saline or cold water. The cold water required less volume to dissolve the gel than the room temperature saline (20 mL vs. 35 mL).

Example 5

In Vivo Experiments

Independently two adult female pigs were anesthetized. In each a lower midline incision was made, the left ureter isolated, a ureterotomy performed adjacent to the bladder and a guide wire was advanced up the ureter to the kidney. A stone was then pushed up the ureter to approximately 10 cm proximal to the ureterotomy. A rigid ureteroscope (Stortz) was passed up the ureter, the stone visualized, a 3 French catheter passed through the ureteroscope beyond the stone, a cooled 20 w % solution of purified poloxamer 407 injected, the catheter removed and the electro hydraulic probe passed to the stone through the ureteroscope. The stone was successfully fragmented with no fragments progressing proximally. The ureter was surgically removed, and pathological examination revealed a reactive epithelium consistent with manipulation by the ureteroscope. The animals were euthanized. In sum, in both experiments, the stones were successfully fragmented without any discernable untoward effects to the ureters.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of mitigating risk of damage to surrounding body tissue during lithotripsy on a concretion located in a lumen of the body, the method comprising:
   introducing a solution comprising purified inverse thermosensitive polymer at a location distal to the concretion in the lumen;
   forming a temporary plug in the lumen distal to the concretion by gellation of the solution;
   deploying an energy source proximate to the concretion; and
   applying energy to the concretion with the energy source sufficient to fragment the concretion and propel one or more fragments of the concretion into the distal, temporary plug; wherein the temporary plug is configured such that it is capable of withstanding impact with fragments of the concretion and prevent further migration of the fragments down the lumen beyond the location of the temporary plug, the concretion is not contained, partially or completely, within the temporary plug prior to the application of energy thereto, and wherein the inverse thermosensitive polymer is a purified poloxamer or poloxamine.

2. The method of claim 1, wherein said solution comprising a purified inverse thermosensitive polymer further comprises a contrast-enhancing agent.

3. The method of claim 2, wherein said contrast-enhancing agent is selected from the group consisting of radiopaque materials, paramagnetic materials, heavy atoms, transition metals, lanthanides, actinides, dyes, and radionuclide-containing materials.

4. The method of claim 1, wherein the purified inverse thermosensitive polymer has a molecular weight between 1,000 and 50,000, inclusive.

5. The method of claim 1, wherein the purified inverse thermosensitive polymer has a polydispersity index from about 1.5 to 1.0.

6. A method of mitigating risk of damage to surrounding body tissue during lithotripsy on a concretion located in a lumen of the body, the method comprising:
   introducing a solution comprising an inverse thermosensitive polymer at a location distal to the concretion in the lumen;

forming a temporary plug in the lumen distal to the concretion by gellation of the solution;

deploying an energy source proximate to the concretion; and applying energy to the concretion with the energy source sufficient to fragment the concretion and propel one or more fragments of the concretion into the distal temporary plug; wherein the temporary plug is configured such that it is capable of withstanding impact with fragments of the concretion and prevent further migration of the fragments down the lumen beyond the location of the temporary plug, the concretion is not contained, partially or completely, within the temporary plug prior to the application of energy thereto; and introducing a saline solution sufficient to dissolve the temporary plug.

7. The method of claim 6, wherein the inverse thermosensitive polymer is a purified poloxomer or poloxamine.

8. The method of claim 7, wherein said inverse thermosensitive polymer is selected from the group consisting of purified poloxamine 1107, purified poloxamine 1307, purified poloxamer 338 and purified poloxamer 407.

9. The method of claim 8, wherein said solution comprising an inverse thermosensitive polymer further comprises a contrast-enhancing agent.

10. The method of claim 9, wherein said contrast-enhancing agent is selected from the group consisting of radiopaque materials, paramagnetic materials, heavy atoms, transition metals, lanthanides, actinides, dyes, and radionuclide-containing materials.

11. The method of claim 10, wherein the inverse thermosensitive polymer has a molecular weight between 1,000 and 50,000, inclusive.

12. The method of claim 11, wherein the inverse thermosensitive polymer has a polydispersity index from about 1.5 to 1.0.

13. A method of mitigating risk of damage to surrounding body tissue during extracorporeal lithotripsy on a concretion located in a lumen of the body of a patient, the method comprising:

introducing a solution comprising an inverse thermosensitive polymer at a first location distal to the concretion in the lumen;

introducing said solution at a second location in the lumen, wherein said second location is on a side of the concretion that is approximately opposite the first location of the solution;

forming two temporary plugs in the lumen spaced from the concretion by gelation of the solution;

deploying an energy source proximate to the concretion from outside the body of the patient;

applying energy to the concretion sufficient to fragment the concretion, wherein the two temporary plugs are configured such that they are capable of withstanding impact with fragments of the concretion and prevent further migration of the fragments down the lumen beyond the location of the temporary plugs, and the concretion is not contained, partially or completely, within the temporary plugs prior to the application of energy thereto.

14. The method of claim 13, wherein the inverse thermosensitive polymer is a purified poloxomer or poloxamine.

15. The method of claim 14, wherein said inverse thermosensitive polymer is selected from the group consisting of purified poloxamine 1107, purified poloxamine 1307, purified poloxamer 338 and purified poloxamer 407.

16. The method of claim 15, wherein said solution comprising an inverse thermosensitive polymer further comprises a contrast-enhancing agent.

17. The method of claim 16, wherein said contrast-enhancing agent is selected from the group consisting of radiopaque materials, paramagnetic materials, heavy atoms, transition metals, lanthanides, actinides, dyes, and radionuclide-containing materials.

18. The method of claim 17, wherein the inverse thermosensitive polymer has a molecular weight between 1,000 and 50,000, inclusive.

19. The method of claim 18, wherein the inverse thermosensitive polymer has a polydispersity index from about 1.5 to 1.0.

20. The method of claim 13 further comprising introducing a saline solution sufficient to dissolve the two temporary plugs.

* * * * *